US008980342B2

(12) United States Patent
Lemaire et al.

(10) Patent No.: US 8,980,342 B2
(45) Date of Patent: Mar. 17, 2015

(54) ANTIOXIDANT AND PHYSICAL PERFORMANCE EFFECTS OF A GRAPE EXTRACT

(75) Inventors: Benoit Lemaire, Moulon (FR); Sophie Lafay, Montagne (FR); Alvin Ibarra, Hoboken, NJ (US); Marc Roller, Morieres les Avignon (FR); Jacques DiKansky, Avignon (FR)

(73) Assignee: Naturex, S.A., Avignon (FR)

( * ) Notice: Subject to any disclaimer, the term of this patent is extended or adjusted under 35 U.S.C. 154(b) by 1263 days.

(21) Appl. No.: 12/195,303

(22) Filed: Aug. 20, 2008

(65) Prior Publication Data

US 2010/0047372 A1 Feb. 25, 2010

(51) Int. Cl.
*A61K 36/87* (2006.01)
*A61K 36/00* (2006.01)

(52) U.S. Cl.
CPC ....................................... *A61K 36/87* (2013.01)
USPC .......................................... 424/766; 424/725

(58) Field of Classification Search
None
See application file for complete search history.

(56) References Cited

U.S. PATENT DOCUMENTS

| 6,470,894 | B2 | 10/2002 | Hersh et al. | |
|---|---|---|---|---|
| 2003/0143311 | A1* | 7/2003 | Gillota | 426/590 |
| 2004/0170709 | A1* | 9/2004 | Hastings et al. | 424/757 |
| 2004/0247714 | A1* | 12/2004 | Roe et al. | 424/766 |
| 2006/0088643 | A1 | 4/2006 | Fugal et al. | |
| 2008/0044539 | A1 | 2/2008 | Perlman et al. | |

FOREIGN PATENT DOCUMENTS

DE 10006837 A1 * 8/2001

OTHER PUBLICATIONS

Kohler et al, Preparative isolation of procyanidins from grape seed extracts by high-speed counter-current chromatography, Journal of Chromatrography A, 1177 (2008) 114-125.*
Oszmianski et al, Fractionation and identification of some low molecular weight grape seed phenolics. Journal of Agricultural and Food Chemistry (1989), vol. 37, No. 5, pp. 1293-1297.*
WO, PCT/US20096/053905—International Search Report, Oct. 13, 2009.
Lemaire B. and Lafay S., *Powergrape—The grape extract rich in procyanidins which reduce exercise-induced oxidative stress of professional soccer players*, Berkem® developpment, Le Marais Quest, 24680 Gardonne, France, 2006.

* cited by examiner

*Primary Examiner* — Qiuwen Mi
(74) *Attorney, Agent, or Firm* — Matthias Scholl, PC; Matthias Scholl

(57) ABSTRACT

A method of enhancing physical performance during exercise by administering an amount of a grape extract effective to treat a subject. A preferred grape extract comprises a concentration of flavanol monomers of greater than about 5% by weight, and more preferably within a range from about 12% by weight to about 50% by weight, and a concentration of flavanol dimers preferably greater than about 2% by weight, and more preferably within a range from about 6% by weight to about 20% by weight. The flavanol monomers preferably include catechin, epicatechin, epicatechin gallate, and gallic acid. The flavanol dimers preferably include procyanidin B1, procyanidin B2, procyanidin B3, procyanidin B4, and procyanidin B2-O-gallate.

6 Claims, 15 Drawing Sheets

ANTIOXIDANT AND PHYSICAL PERFORMANCE EFFECTS OF A GRAPE EXTRACT

FIELD OF THE INVENTION

The present invention relates to the use of grape extracts, such as Powergrape™ grape extract manufactured by NATUREX, that contain a high content of bioavailable polyphenols to increase antioxidant level and performance during physical exercise.

BACKGROUND OF THE INVENTION

Physical exercise is characterized by an increase in oxygen consumption by the whole body. During oxygen metabolism, much of the oxygen consumed is bound to hydrogen during oxidative phosphorylation forming water. However, 4% to 5% of the oxygen consumed during respiration is not completely reduced to water, instead forming free radicals. Thus, the increase of oxygen consumption during an athletic competition generates a concomitant increase of free radical production and creates molecular cell damage such as peroxidation of lipids.

Many studies on animals and humans showed that polyphenols, vegetal secondary metabolites, are antioxidants and could decrease oxidative stress and the risk of associated diseases. Grape extracts rich in flavanols and particularly in procyanidine, such as Powergrape™ grape extract, are known to be good antioxidants in vitro and in vivo. Supplementation with grape extracts rich in flavanols and procyanidins has been shown to decrease oxidative stress induced by athletic competition in professional soccer players.

In one study aimed at determining if the grape extract (Powergrape™ grape extract, NATUREX) supplementation is able to decrease oxidative stress generated in professional athletes during a competition period, 200 mg of grape extract was administrated twice daily (400 mg/day) over 21 days to 7 professional soccer players. The experimental design was a longitudinal study without a placebo group. Plasma biomarkers of oxidative stress and antioxidant status were determined during a competition period, before (day 0) and after (day 21) grape extract supplementation. Blood parameters measured were Vitamin C, ascorbyl radical, Vitamin E, cholesterol, reduced glutathione (GSH), oxidized glutathione (GSSG), superoxide dismutase (SOD), glutathione peroxidase (GPx), thiol proteins, total hydrophilic antioxidant capacity, total lipophilic antioxidant capacity, and coenzyme $Q_{10}$ (ubiquinone).

Results showed that the lipophilic antioxidant capacity was increased, so the total antioxidant capacity was also enhanced. The levels of glutathione (GSH) and oxidized glutathione (GSSH) were decreased, so the ratio of GSH/GSSH is normalized. The enzymes glutathione peroxidase (GPx) and superoxide dismutase (SOD) were decreased. An increase in coenzyme $Q_{10}$ (ubiquinone) was observed. Vitamin C was strongly enhanced, by more than 60%, and its ratios with Vitamin E (Vitamin C/Vitamin E) and ascorbyl radical (Vitamin C/ascorbyl radical) were significantly increased. Results of this experiment are shown in Table 1 and FIG. 1.

TABLE 1

Effects of grape extract (Powergrape ™ grape extract, NATUREX) on parameters of oxidative stress and antioxidant capacity in professional athletes in pre and post treatment (21 days).

|  | Reference values | Pre-treatment D0 Mean +/− SD | Post-treatment D21 Mean +/− SD | Unity |
| --- | --- | --- | --- | --- |
| Vitamin C | 6.21-15.18 | 9.50 +/− 1.45 | 15.16 +/− 3.91 | µg/mL |
| Radical ascorbyl | 0.28-0.44 | 0.40 +/− 0.07 | 0.51 +/− 0.10 | / |
| VitC/Radical ascorbyl | 18.84-36.20 | 24.32 +/− 5.32 | 30.59 +/− 7.88 | / |
| Vitamin E | 8-15 | 13.21 +/− 2.47 | 13.43 +/− 3.61 | µg/mL |
| Cholesterol | 1.4-2.00 | 2.06 +/− 0.47 | 2.03 +/− 0.38 | g/L |
| VitE/cholesterol | 4.4-7.00 | 6.44 +/− 1.13 | 6.62 +/− 1.15 | / |
| VitC/VitE ratio | >1.3 | 0.75 +/− 0.21 | 1.20 +/− 0.48 | / |
| Reduced glutathion (GSH) | 753-958 | 1300.74 +/− 207.99 | 1010.56 +/− 164.27 | µmol/L |
| Oxidized glutathion (GSSG) | 1.17-5.32 | 27.03 +/− 21.14 | 3.34 +/− 1.41 | µmol/L |
| GSH/GSSG ratio | 156-705 | 93.94 +/− 79.94 | 341.97 +/− 135.61 | / |
| Superoxyde dismutase (SOD) | 785-1570 | 1755.43 +/− 367.01 | 1138.43 +/− 216.96 | UI/g Hb |
| Gluhathion peroxidase (GPx) | 30-55 | 56.57 +/− 7.09 | 42.86 +/− 13.36 | UI/g Hb |
| Thiols proteins | 310.14-523.86 | 418.19 +/− 15.41 | 445.55 +/− 52.55 | µmol/L |
| Hydrophilic antioxidant capacity | 138-334 | 225.00 +/− 56.57 | 199.29 +/− 70.20 | nmol eq aa/mL |
| Lipophilic antioxidant capacity | 47-74 | 59.64 +/− 6.15 | 67.83 +/− 4.49 | nmol eq Trolox/mL |
| Coenzyme $Q_{10}$ (Ubiquinone) | 0.4-1.2 | 0.48 +/− 0.13 | 0.94 +/− 0.29 | µg/mL |

SUMMARY OF THE INVENTION

Until now the use of grape extracts has not been known to have any effect on physical performance during exercise, specifically improving physical performance. The present invention provides methods of using grape extracts to enhance physical performance during exercise and to enhance recovery after physical exercise.

In one embodiment of the invention, the grape extract comprises a concentration of flavanol monomers of greater than about 5% by weight, and preferably within a range from about 12% by weight to about 50% by weight. In one embodiment of the invention, the grape extract comprises a concentration of flavanol monomer of about 12% by weight.

In another embodiment of the invention, the grape extract comprises a concentration of flavanol dimers of greater than about 2% by weight, and preferably within a range from about 6% by weight to about 20% by weight. In one embodiment of the invention, the grape extract comprises a concentration of flavanol dimers of about 6% by weight.

The flavanol monomer molecules preferably comprise one or more of catechin, epicatechin, epicatechin gallate, and gallic acid. In one embodiment of the invention, the flavanol monomer molecules comprise all of catechin, epicatechin, epicatechin gallate, and gallic acid. The flavanol dimers preferably comprise one or more of procyanidin B1, procyanidin B2, procyanidin B3, procyanidin B4, and procyanidin B2-O-gallate. In one embodiment of the invention, the flavanol dimer molecules comprise all of procyanidin B1, procyanidin B2, procyanidin B3, procyanidin B4, and procyanidin B2-O-gallate.

In one embodiment of the invention, the grape extract includes from about 5% to about 50% flavanol monomers by weight and from about 2% to about 20% flavanol dimers by weight. It has been found that the application of grape extract in accordance with the present invention has a number of salutatory effects, in addition to improving athletic performance during exercise, and separately to improving recovery after exercise. These include, among other things, the following:

Improving antioxidant status and decreasing oxidative stress induced by physical exercise.
Increasing the concentrations of lipophilic, hydrophilic and total antioxidant capacity during physical exercise.
Increasing ORAC value during physical exercise.
Limiting a decrease in FRAP capacity during physical exercise.
Decreasing the concentration of urinary isoprostanes during physical exercise.
Improving an antioxidant Vitamin E and Vitamin C balance during physical exercise.
Increasing the concentration of Vitamin C during physical exercise.
Increasing the concentration of Vitamin E during physical exercise.
Increasing the ratio of Vitamins C/E during physical exercise.
Increasing the Vitamin C/Ascorbyl radical ratio during physical exercise.
Increasing the ratio of Vitamins E/Cholesterol during physical exercise.
Increasing the concentration of coenzyme $Q_{10}$ (ubiquinone) during physical exercise.
Improving antioxidant enzymatic status during physical exercise.
Decreasing levels of glutathione (GSH) and oxidized glutathione (GSSH) and normalizing the ratio of GSH/GSSH during physical exercise.
Limiting decreases of glutathione peroxidase (GPx) during physical exercise.
Decreasing levels of superoxide dismutase (SOD) during physical exercise.
Improving oxygen delivery by enhancing hemoglobin and red cell quality during physical exercise.
Maintaining bioavailability of iron during physical exercise.
Improving the quality of red blood cells during physical exercise.
Increasing the concentration of hemoglobin during physical exercise.
Maintaining ferritin concentrations at pre-exercise levels during physical exercise.
Decreasing the level of creatine phosphokinase (CPK) during physical exercise and thereby reducing a risk of muscular damage.
Increasing the explosive strength capacity during physical exercise.
Improving the physical performance in an anaerobic condition with presence of a lactic acid.
Increasing recovery after physical exercise.

Until now, the consequences of administering grape extract had not been associated with a demonstrated improvement in physical performance during exercise or recovery after exercise.

It should be understood that for a given mammal the efficacious dose to be administered in a given application will be determined, in accordance with the abilities of a person of ordinary skill in the art, based on the body mass of the animal consuming the grape extract and the animal's ability to respire/absorb the grape extract constituents. It has been found that for humans having a weight of 65 to 120 kg an effective dose of 400 mg per day, more preferably delivered in 2 equal doses, is sufficient to achieve the results of the invention.

BRIEF DESCRIPTION OF THE DRAWINGS

Further features, advantages and characteristics of the present invention will become apparent to a person of ordinary skill in the art in view of the following detailed discussion of preferred embodiments of the present invention, made with reference to the drawings annexed, in which.

DETAILED DESCRIPTION OF THE INVENTION

Figure 1:
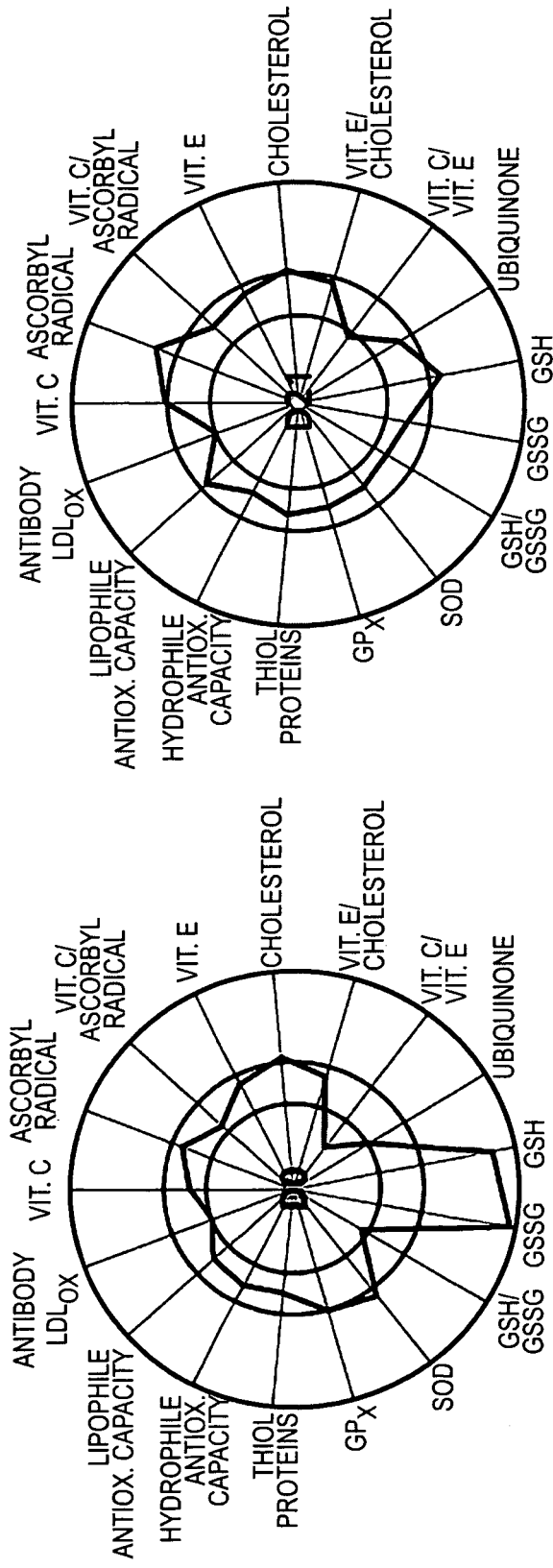
FIG. 1 illustrates a prior art study of the effects of a preferred grape extract on oxidative stress and antioxidant capacity in professional athletes in pre and post treatment (21 days), in which optimal values are shown in the inner ring.

In the preferred embodiment, the grape extract is obtained from *Vitis vinifera* L. (Vitaceae). The extraction is made with a hydroalcoholic solvent and a subsequent purification with ethyl acetate. The native extract obtained after filtration and vacuum concentration is preferably dried using a conventional spray-dryer. The grape extract in powder form contains mainly flavanols and more particularly oligomeric procyanidins (OPCs). Typically, the extract contains more than 90% of total polyphenols. The content of OPCs in the grape extract is around 50%. The extract usually presents about 12% of flavanol monomers and about 6% of flavanol dimers. Flavanol monomers include catechin, epicatechin, and epicatechin-O-gallate. Gallic acid, a phenolic acid, also can be counted as a flavanol monomer because it naturally occurs with OPCs. Flavanol dimers include procyanidins B1, B2, B3, B4 and B2-O-gallate. Other components in the grape extract are soluble sugars, proteins, lipids and minerals. Flavanol monomers and dimers are known to have a high bioavailability in comparison to high molecular weight procyanidins. Monomers and dimers are absorbed in the upper part of the digestive tract while high molecular weight procyanidins need to be metabolized by the microflora in the colon to be absorbed.

During an intense physical activity or overload training, the antioxidant capacity of the organism is not sufficient to limit free radical production, resulting in an increase of oxidative stress that can be detrimental to the body. The detrimental effect in the body caused by the oxidative stress may involve unbalanced non-enzymatic/enzymatic antioxidant status, and cellular and muscular damages.

The antioxidant status in the body can be evaluated using global oxidant methods, such as oxygen radical absorbance capacity (ORAC), and ferric reducing/antioxidant power (FRAP). This evaluation can be easily conducted directly on the grape extract or on the blood samples of individuals supplemented with the grape extract.

The oxidative stress can be evaluated by determination of urinary isoprostanes, which are very well correlated with the oxidative and inflammatory status of the body.

To determine the effect of grape extract on non-enzymatic and enzymatic antioxidant status, different biomarkers can be employed. Non-enzymatic biomarkers include Vitamin C, ascorbyl radical, Vitamin E, and coenzyme $Q_{10}$ (ubiquinone). The Vitamin C/Vitamin E ratio represents the balance between the hydrophilic and lipophilic non-enzymatic antioxidant capacity in the organism, and has to be maintained in normal levels especially during physical exercise. Low values of this ratio are indicative of cardiovascular risk. The Vitamin C/ascorbyl radical ratio indicates the level of oxidized Vitamin C, therefore, it is desirable to increase this ratio during physical exercise. Cholesterol can also be affected by the oxidative balance in the organism. The Vitamin E/cholesterol ratio represents the capacity of Vitamin E to protect cholesterol. Coenzyme $Q_{10}$ (ubiquinone), is considered as an antioxidant because of its ability to transfer electrons, and therefore increasing its level in plasma helps to protect the body against oxidative stress damages.

Enzymatic biomarkers include superoxide dismutase (SOD), glutathione (GSH), oxidized glutathione (GSSH), and glutathione peroxidase (GPx). Superoxide dismutase (SOD) in an antioxidant enzyme implicated in the protection against primary free radical, oxygen reactive species. Therefore, one of the targets in the supplementation of athletes is to limit the reduction of SOD in the body during physical exercise. Moreover, glutathione and oxidized glutathione are co-factors of glutathione peroxidase (GPx), an antioxidant enzyme implicated in the protection against secondary free radicals, preventing lipid peroxidation. In the organism, especially during physical exercise, the ratio GSH/GSSH has to be increased to protect the body. In fact, athletes during competition significantly reduce this ratio as well as the level of glutathione peroxidase (GPx). For this reason, it is also desirable to prevent the decrease of glutathione peroxidase (GPx) during physical exercise.

The capacity to deliver oxygen in the body during exercise is another important factor for improving physical performance. Red blood cells are the principal means of delivering oxygen from the lungs or gills to body tissues via the blood. Therefore, it is desirable to improve the quality and quantity of red blood cells in plasma to increase the disposal of oxygen. Red blood cells can be damaged by oxidative stress. The High Resolution Blood Morphology (HRBM) test is useful to assess any morphological change and improvement of patients during a course of disease. This method allows assessment of the oxidative stress profile and monitoring of physiological and morphological changes during treatment.

During physical exercise, the concentration of iron in the body may be decreased. Moreover, it has been proposed that OPCs may decrease iron absorption, exacerbating the effect of physical exercise. Therefore, to develop a suitable botanical supplement for enhancing physical performance, it is important to verify that the supplement does not modify the concentration of the main transporters of iron in the body. These principal transporters are ferritin and hemoglobin.

Creatine phosphokinase (CPK), or creatine kinase (CK), is an enzyme implicated in the storage of energy in the muscles, where CPK naturally occurs. During physical exercise, the oxidative stress increases cell damage causing the release of CPK in plasma. For that reason, plasmatic creatine phosphokinase (CPK) is also used as a biomarker to evaluate muscular damage. Therefore, it is desirable to have low levels of CPK in plasma during physical exercise.

The physical performance, expressed as explosive strength, performance in anaerobic condition with presence of lactic acid, and recovery, can be measured using the Optojump® system. Optojump® (Microgate, Bolzano, Italy) is an optical measurement system designed to measure contact and flight times with an accuracy of $\frac{1}{1000}$ of a second during the performance of a series of jumps. The system consists of a series of transmitter and receiver units (known as "springboards") which can be placed up to 3 m apart and parallel to each another. Each 1 m transmitter unit contains 32 light emitting diodes (LEDs) which are positioned 3 mm from ground level at 31.115 mm intervals. The "walkjump" acquisition facility in the Optojump® 3.0 software displays real-time step length, speed and acceleration calculations for each individual stride during a running trial. The uniqueness of this system to display step-by-step stride length estimates in real-time also increases its potential appeal to motor control theorists when evaluating gait regulation during the approach run phase of sports activities.

In the Optojump® test, volunteers are asked to jump as high and as fast as they can during 45 seconds. This test allows evaluation of the physical performance. During these 45 seconds, volunteers are also asked to give their best jumps in terms of height, during the first ten jumps. This first period of the test allows calculating the explosive strength. Also, during these 45 seconds, volunteers are asked to maintain their maximum height during the last five jumps. These last five jumps permit assessment of the residual repetitive explosivity, which is the most significant measure of recovery.

EXAMPLES

Example 1

Nutritional Profiles of the Grape Extract
(Powergrape™ Grape Extract, NATUREX)

Nutritional analyses were conducted according to the European pharmacopoeia. Table 2 shows the nutritional value of the grape extract used in the examples reported herein (Powergrape™ grape extract, NATUREX).

TABLE 2

Nutritional profile of the grape extract (Powergrape ™ grape extract, NATUREX).

| | |
|---|---|
| Loss of drying [JO Mar. 11, 1977] | 3.50% |
| Proteins (Nx6.25) [JO Mar. 11, 1977] | 1.40% |
| Lipids [JO Mar. 11, 1977] | 0.30% |
| Ash [JO Mar. 11, 1977] | 1.38% |
| Soluble sugars [JO Mar. 11, 1977] | 3.00% |
| Total polyphenols [Folin-Ciocalteau] | 90.42% |
| Including flavanol monomers [HPLC] | 12.00% |
| Including flavanol dimers [HPLC] | 6.00% |
| TOTAL | 100.00% |

Example 2

HPLC Chromatogram of the Grape Extract
(Powergrape™ Grape Extract, NATUREX)

Figure 2:
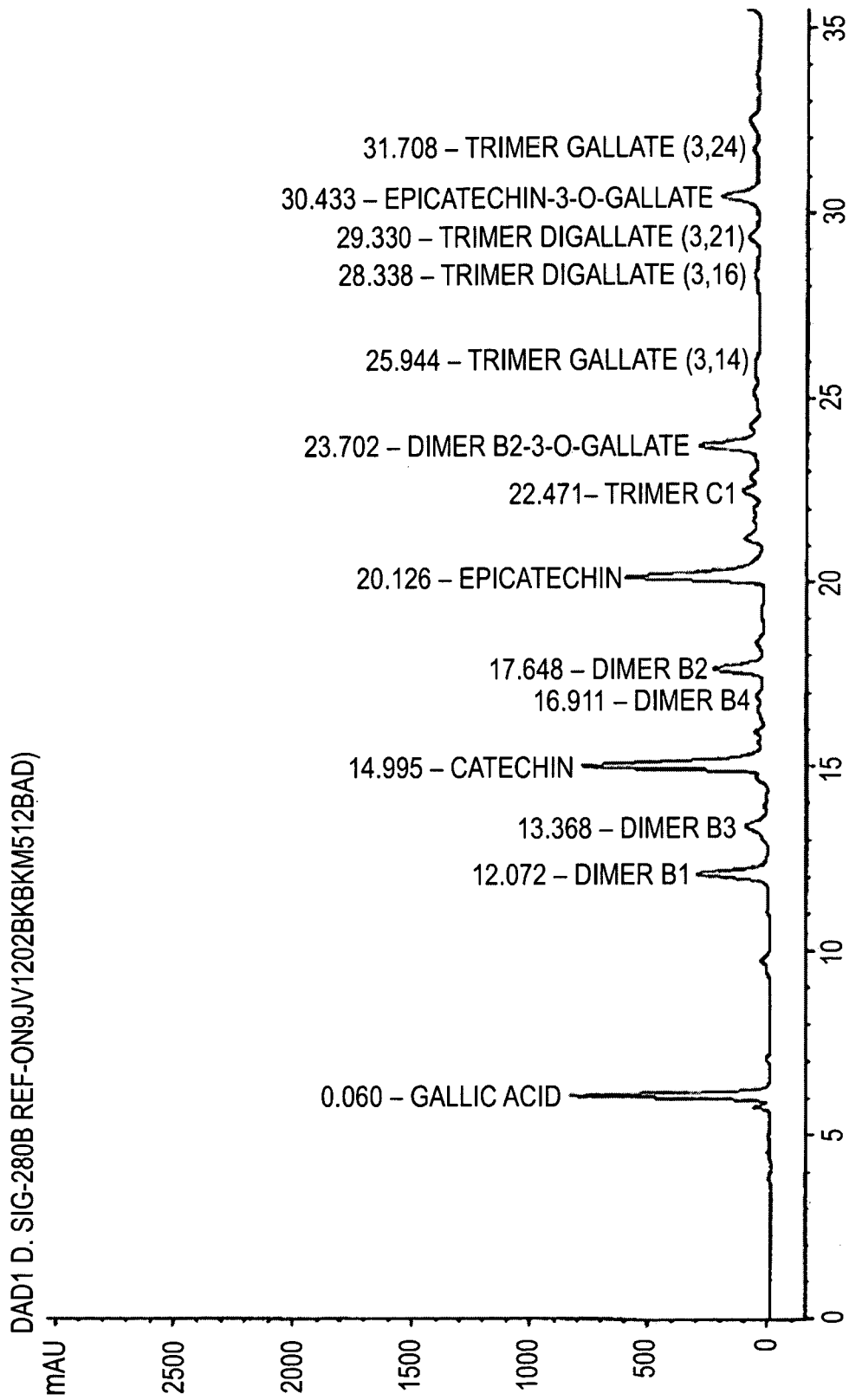
FIG. 2 illustrates an HPLC chemical fingerprint of the grape extract in accordance with a preferred embodiment.

The high-pressure liquid chromatography chemical fingerprint for the whole grape extract is presented in FIG. 2. The method for performing this analysis was as follows: HPLC-DAD was achieved using column $SBC_{18}$ with dimension 250×4.6 mm at 25° C. The flow rate was 0.7 mL/min, and the elution was monitored at 280 nm. The mobile phases were (A) distilled water/trifluoroacetic acid 0.005%, and (B) acetonitrile 65%/trifluoroacetic acid 0.005%. A solution of 85% A by volume and 15% B by volume was maintained for 30 min and then changed to 65% A by volume and 35% B by volume; followed by a linear gradient of 100% B after 32 min total time, maintaining this composition for 9 min; the system was then re-equilibrated to the initial composition. The content of monomers (7 batches) and dimers (4 batches) of grape extract (Powergrape™ grape extract, NATUREX) reported as mean±standard deviation (SD) are shown in Table 3.

TABLE 3

Monomers and dimers content of the grape extract
(Powergrape ™ grape extract, NATUREX)

| Compound | Mean | SD |
|---|---|---|
| Monomers | | |
| Catechin | 5.55 | 1.75 |
| Epicatechin | 5.74 | 1.09 |
| Epicatechin-gallate | 1.78 | 0.54 |
| Gallic acid | 2.51 | 1.33 |
| Dimers | | |
| Procyanidin B1 | 1.60 | 0.18 |
| Procyanidin B2 | 1.91 | 0.15 |
| Procyanidin B3 | 0.75 | 0.02 |
| Procyanidin B4 | 0.48 | 0.10 |
| Procyanidin B2-O-gallate | 1.77 | 0.76 |

Example 3

Antioxidant Value of the Grape Extract
(Powergrape™ Grape Extract, NATUREX): ORAC,
FRAP, and DPPH The oxygen radical absorbance capacities (ORAC) of three batches were determined according to the method described by Cao G, Alessio H M, Cutler R G: "Oxygen-radical absorbance capacity assay for antioxidants." *Free Radic Biol Med;* 14:303-311 (1993) ("Cao et al."). ORAC analyzes were conducted at Lareal Laboratories, France. Total antioxidant power of seven different batches was measured using the ferric reducing/antioxidant power (FRAP) assay. Benzie I F & Strain J J, "The ferric reducing ability of plasma (FRAP) as a measure of "antioxidant power": The FRAP assay *"Anal Biochem* 239(1), 70-6 (1996) ("Benzie and Strain"). FRAP analyses were conducted at NATUREX, France. DPPH radical scavenging activity of seven different batches was measured according to the method described by Brand-Williams W, Cuvelier M E, Berset C., "Use of a free radical method to evaluate antioxidant activity," *Food Science and Technology;* 28(1):25-30 (1995) ("Brand-Williams et al"). DPPH analyzes were conducted at NATUREX, France. Results on ORAC, FRAP and DPPH are shown in Table 4.

TABLE 4

ORAC, FRAP and DPPH values of the grape extract
(Powergrape ™ grape extract, NATUREX).

| Grape extract (Powergrape ™ extract, NATUREX) | Mean | SD |
|---|---|---|
| ORAC (μmol TE/g) (n = 3) | 14,593.00 | 925.00 |
| FRAP (mmol/g) (n = 7) | 7.91 | 0.43 |
| DPPH (μmol TE/g) (n = 7) | 6,952.00 | 919.00 |

Example 4

High Resolution Blood Morphology Test (HRBM)

Figure 3B:
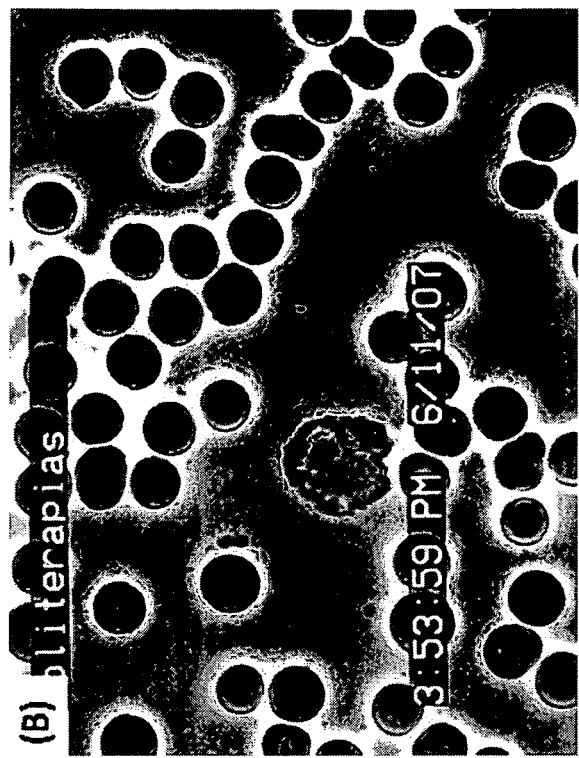
FIG. 3(B) illustrates red blood cells taken from the same subject after consumption of grape extract during 10 days.
Figure 3A:
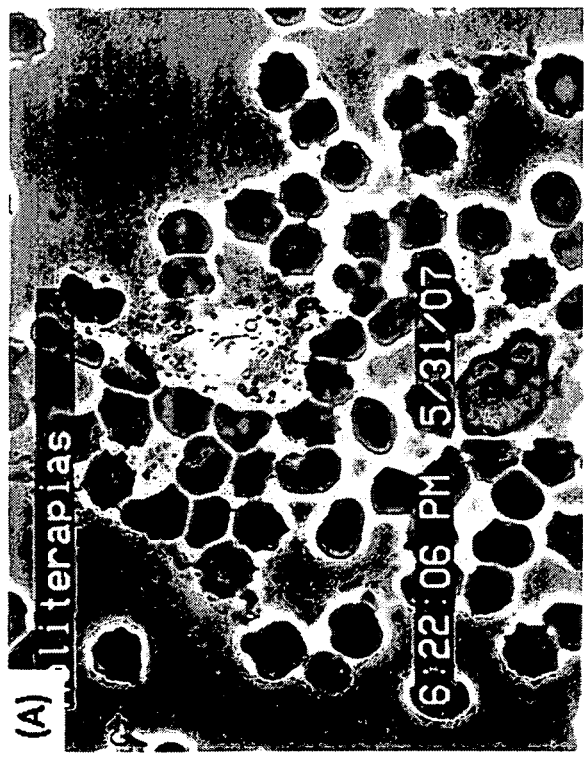
FIG. 3(A) illustrates red blood cells taken from a subject with high oxidative stress level.

A Phase contrast High Resolution Variable Projection Microscope with magnification up to 18.000× that permits observation of tiny particles like mycoplasma of 0.5 microns was used. 400 mg/day of grape extract (Powergrape™ extract, NATUREX) was administrated during 10 days to a volunteer with a high level of oxidative stress caused by organic dysfunctions related to depression, bad dietary habits with high fat intake, digestive disorders, and social stress responsibilities. HRBM test was carried out before and after grape extract administration. FIGS. 3A and 3B show the morphology of the red blood cells with and without administration. The morphology of the red blood cells is significantly better after the grape extract administration, observed as an improvement in the structure of the cell membrane.

Example 5

Effect of the Grape Extract (Powergrape™ Grape Extract, NATUREX) on Oxidative Stress and Antioxidant Capacity in Professional Athletes The aim of this study was to evaluate the effect of the consumption of grape extract (Powergrape™ grape extract, NATUREX) on oxidative stress, antioxidative status, and physical performance and recovery in professional athletes. This study is a randomized, double-blind, placebo (Maltodextrine) controlled, crossover (3 weeks) clinical trial. The subjects were randomly divided in 2 groups. Each group consumed 400 mg of grape extract or placebo at breakfast during one month. At day 0 and day 30 of the supplementation period, blood and urine were sampled from the subjects after they had fasted overnight for more than 10 hours. Additionally, each subject was subjected to an effort test using a validated system Optojump® (Microgate SRL, Bolzano, Italy) associated with a heart rate monitor. The blood parameters tested were oxygen radical absorbance capacity (ORAC), ferric reducing antioxidant power (FRAP), glutathione peroxidase (GPx), Vitamin E, cholesterol, hemoglobin, ferritin, and creatine phosphokinase (CPK). Isoprostanes were measured in urine. The physical parameters explosive strength, performance, and recovery were determined using the Optojump® system.

Figure 4:
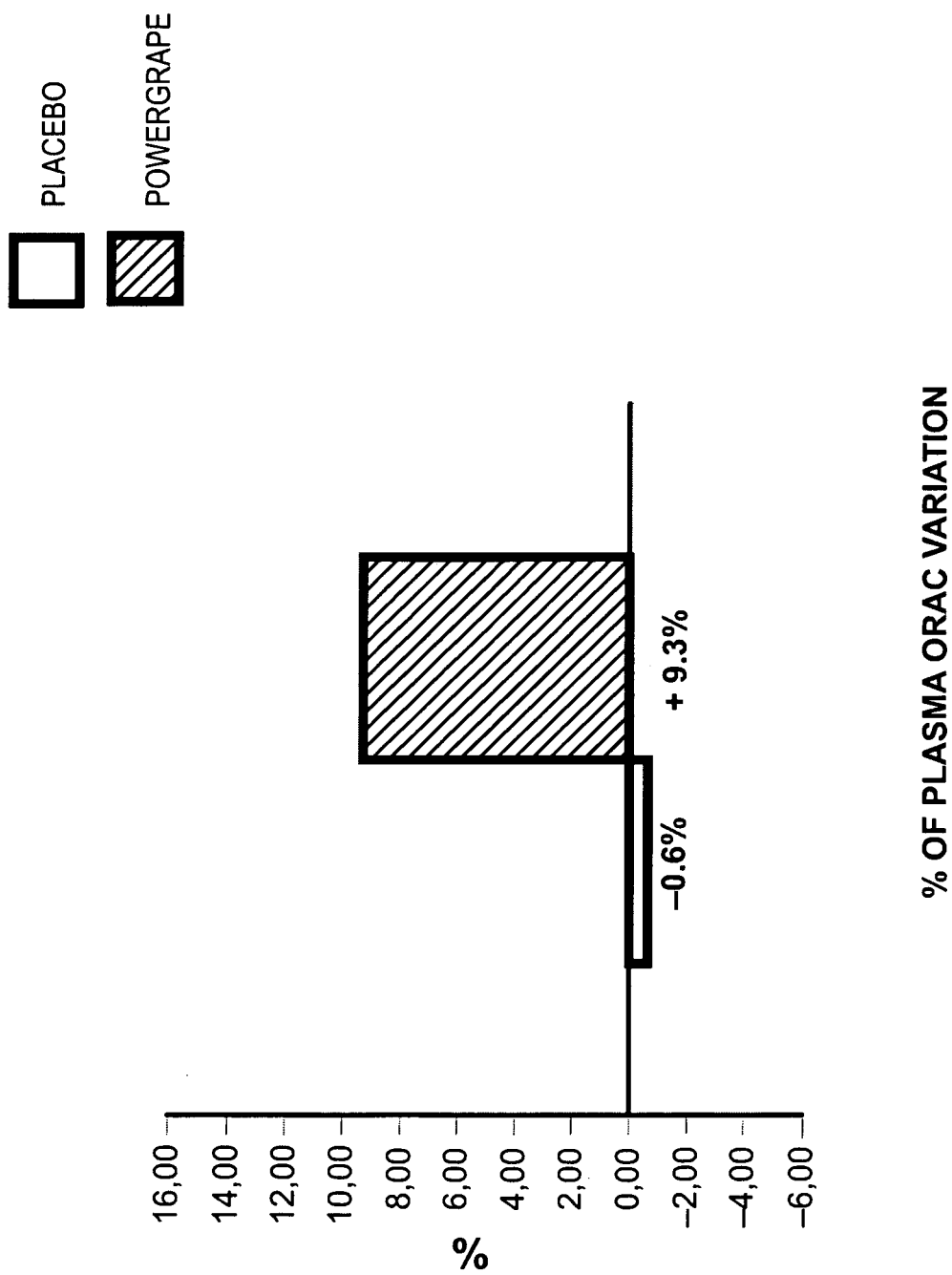
FIG. 4 illustrates a percent of plasma ORAC variation of athlete volunteers after a grape extract supplementation relative to a placebo.
Figure 5:
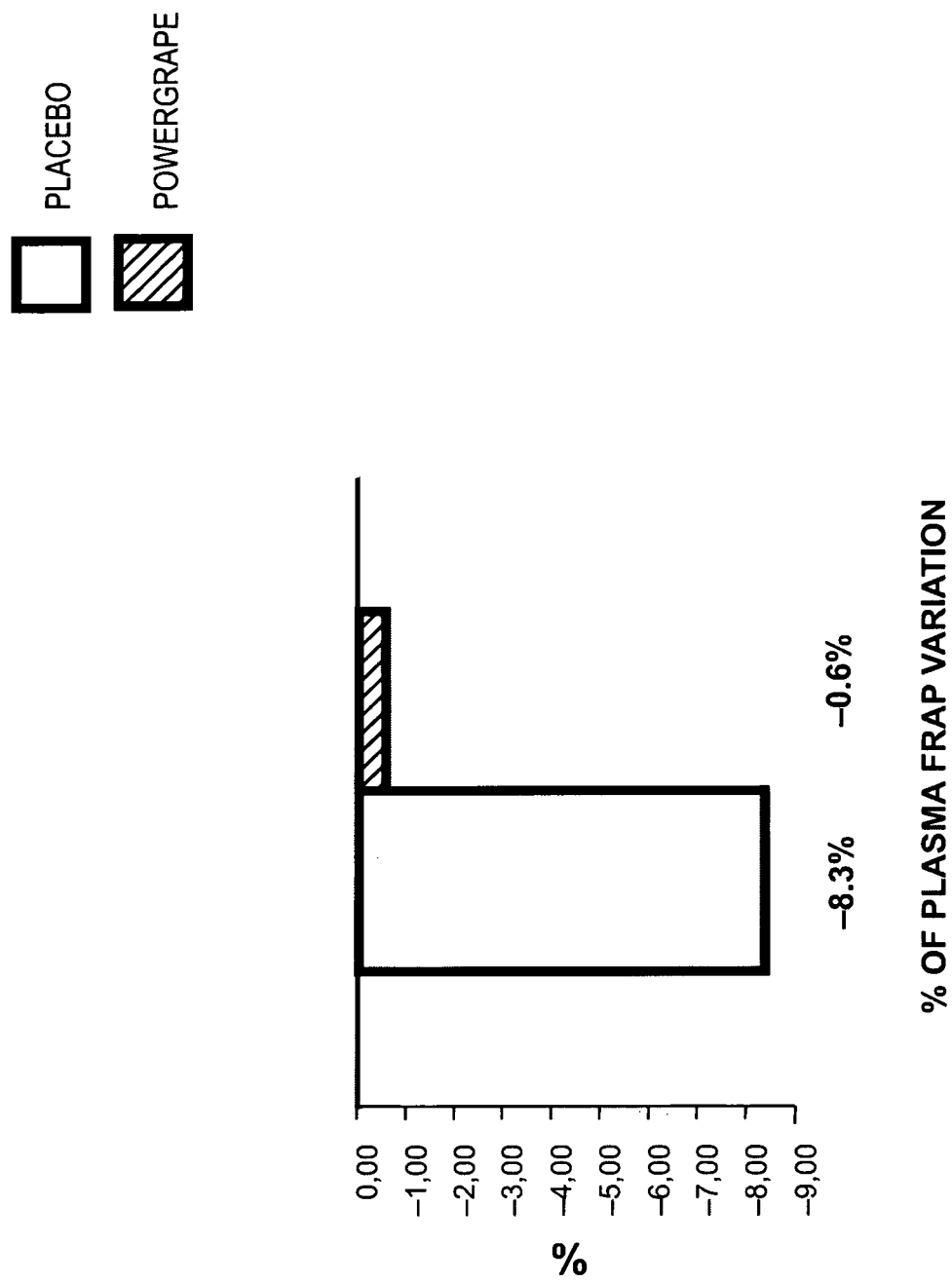
FIG. 5 illustrates a percent of plasma FRAP variation of athlete volunteers after grape extract supplementation relative to a placebo.
Figure 6:
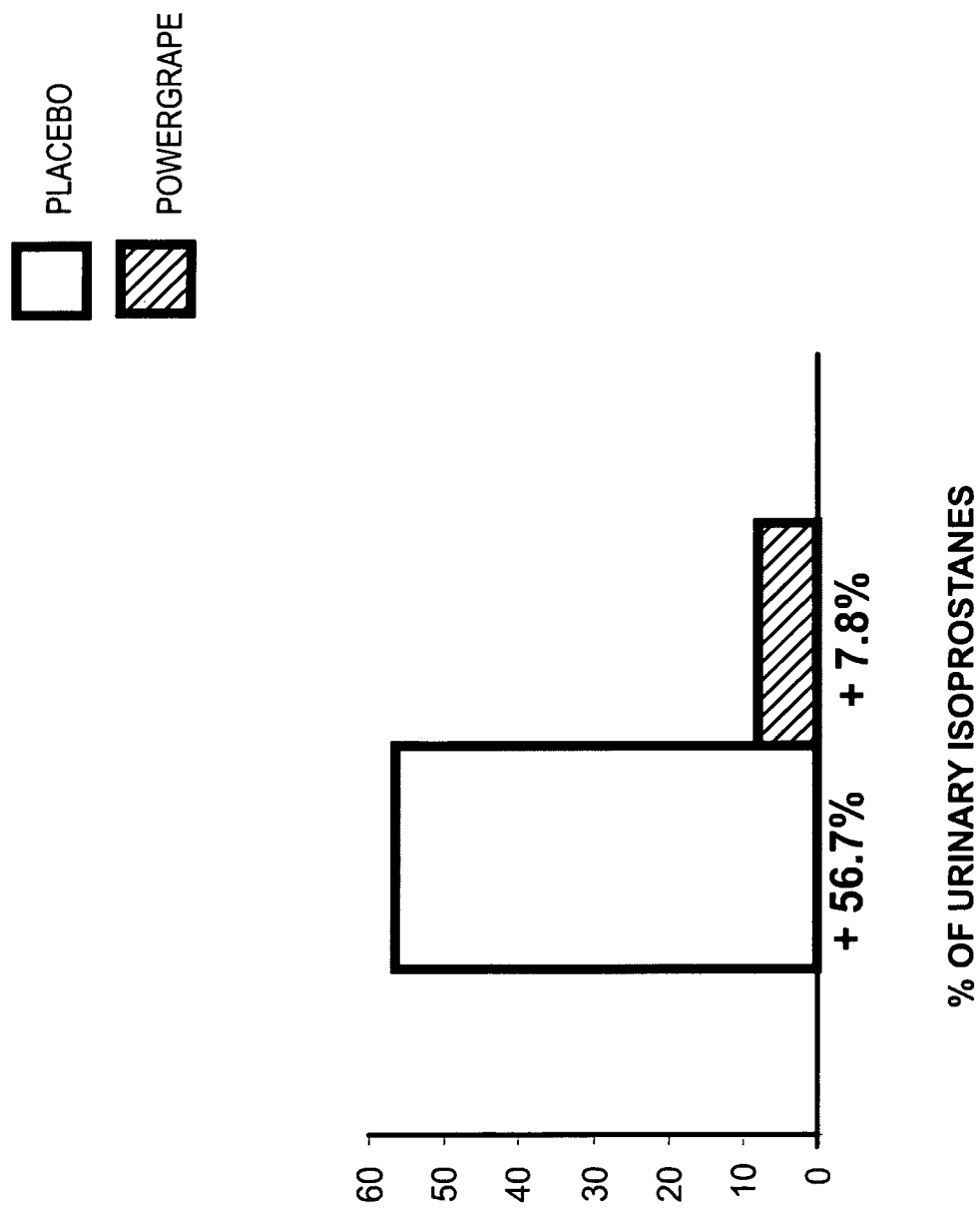
FIG. 6 illustrates a percent of urinary isoprostanes variations of athlete volunteers after grape extract supplementation relative to a placebo.
Figure 7:
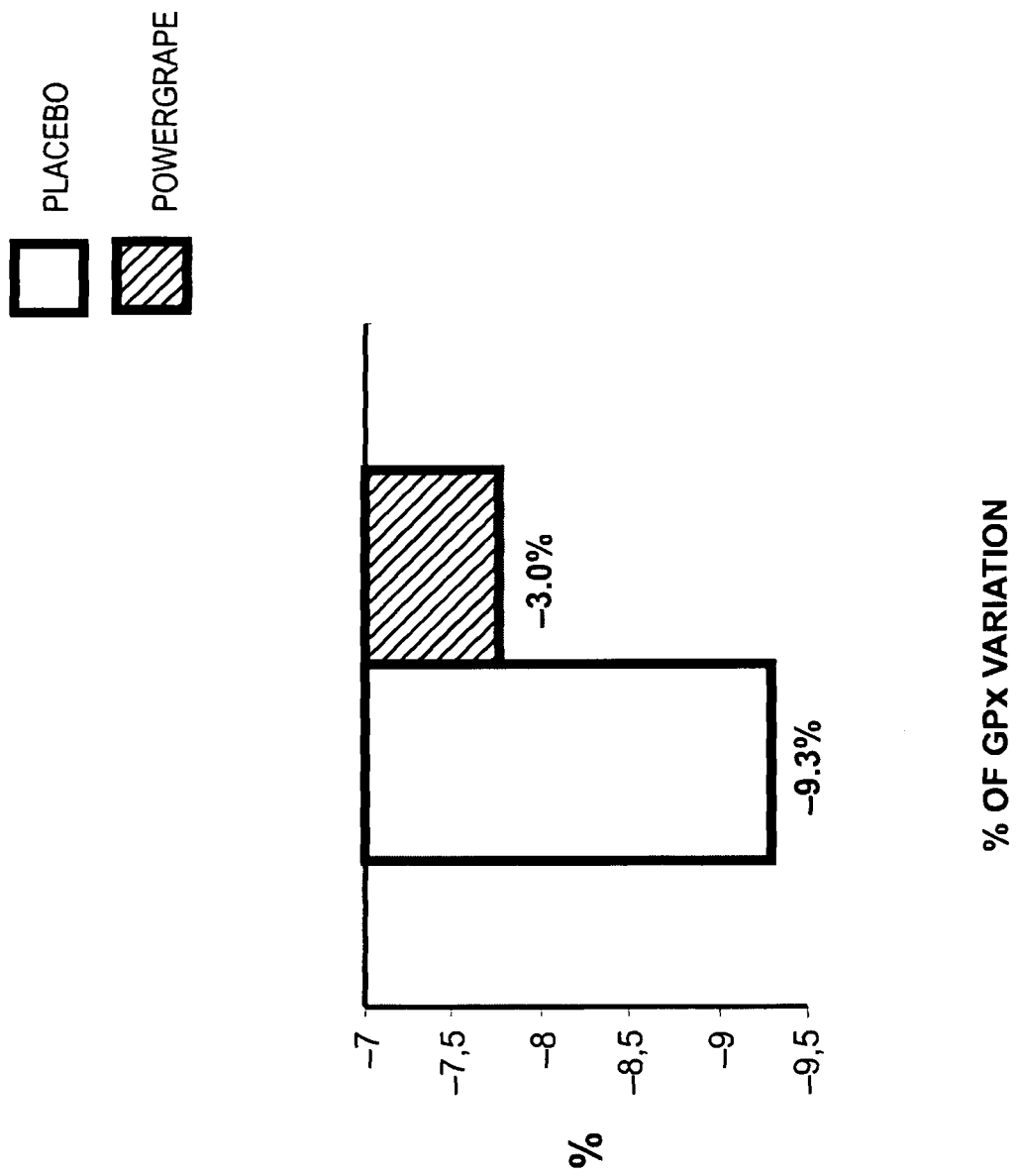
FIG. 7 illustrates a percent of Glutathione peroxidase (GPx) variation of athlete volunteers after grape extract supplementation relative to a placebo.
Figure 8:
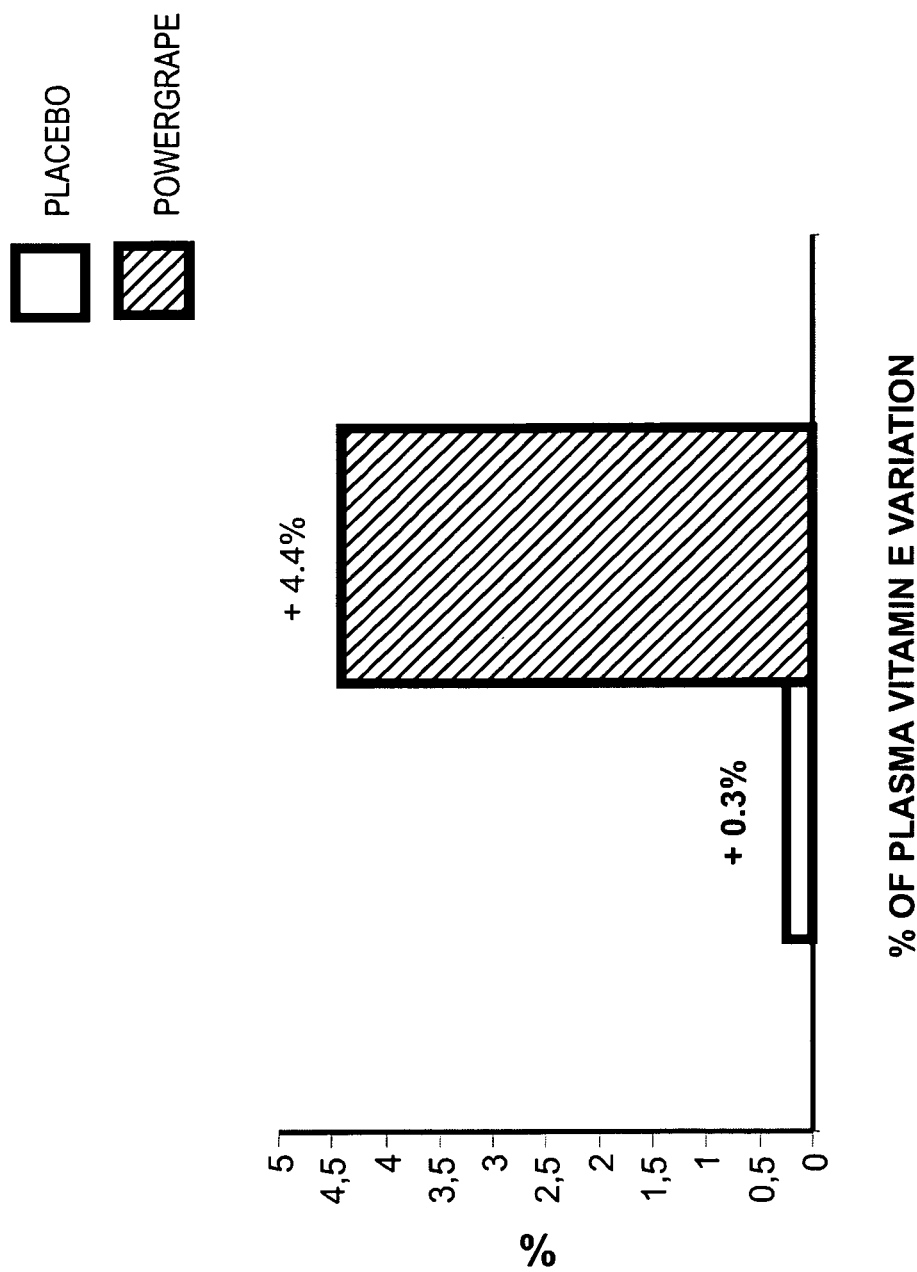
FIG. 8 illustrates a percentage of plasma Vitamin E variation of athlete volunteers after grape extract supplementation relative to a placebo.
Figure 9:
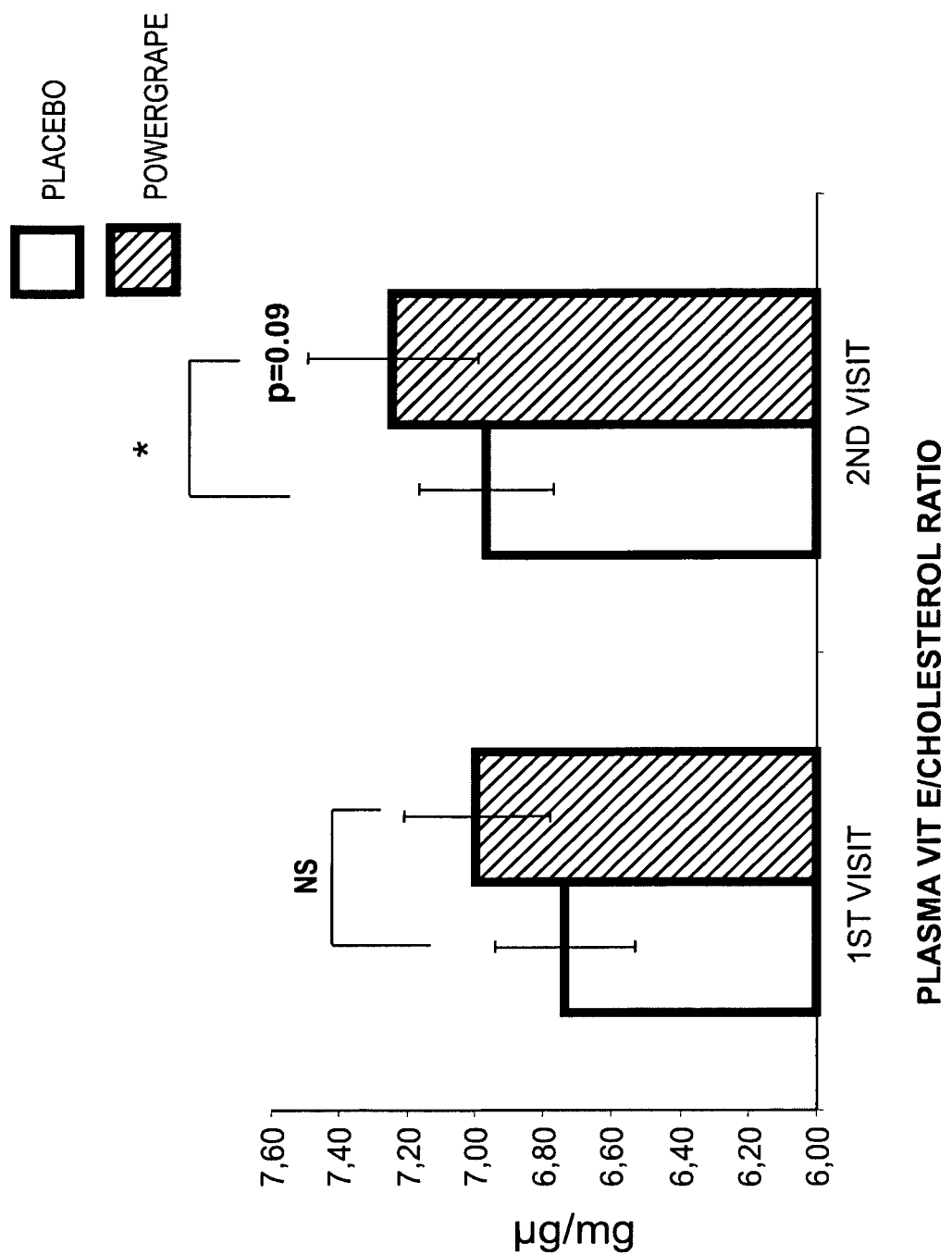
FIG. 9 illustrates a Vitamin E/cholesterol ratio of athlete volunteers before ($1^{st}$ visit) and after ($2^{nd}$ visit) grape extract supplementation relative to a placebo.
Figure 10:
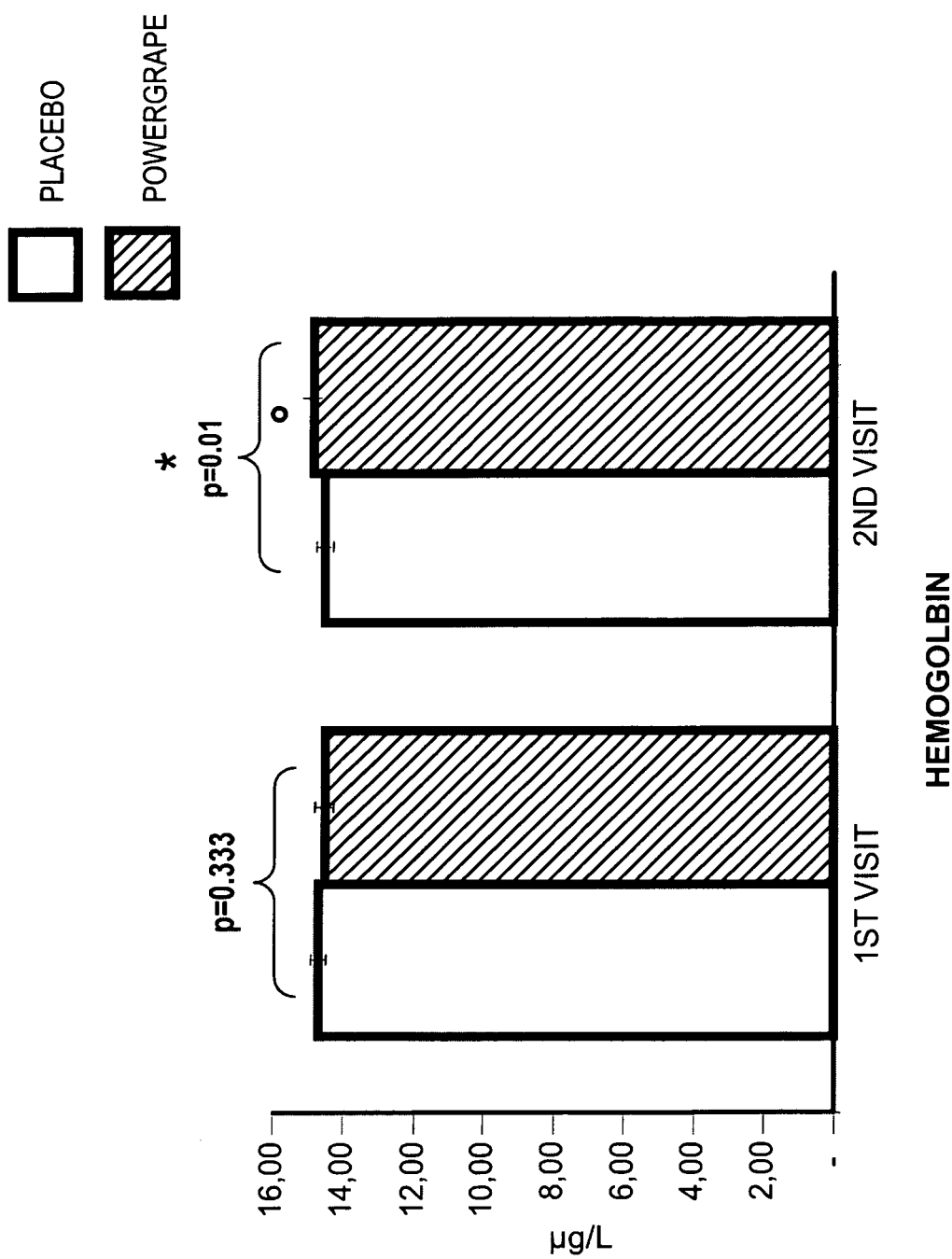
FIG. 10 illustrates a Hemoglobin level in plasma of athlete volunteers before ($1^{st}$ visit) and after ($2^{nd}$ visit) grape extract supplementation relative to a placebo.
Figure 11:
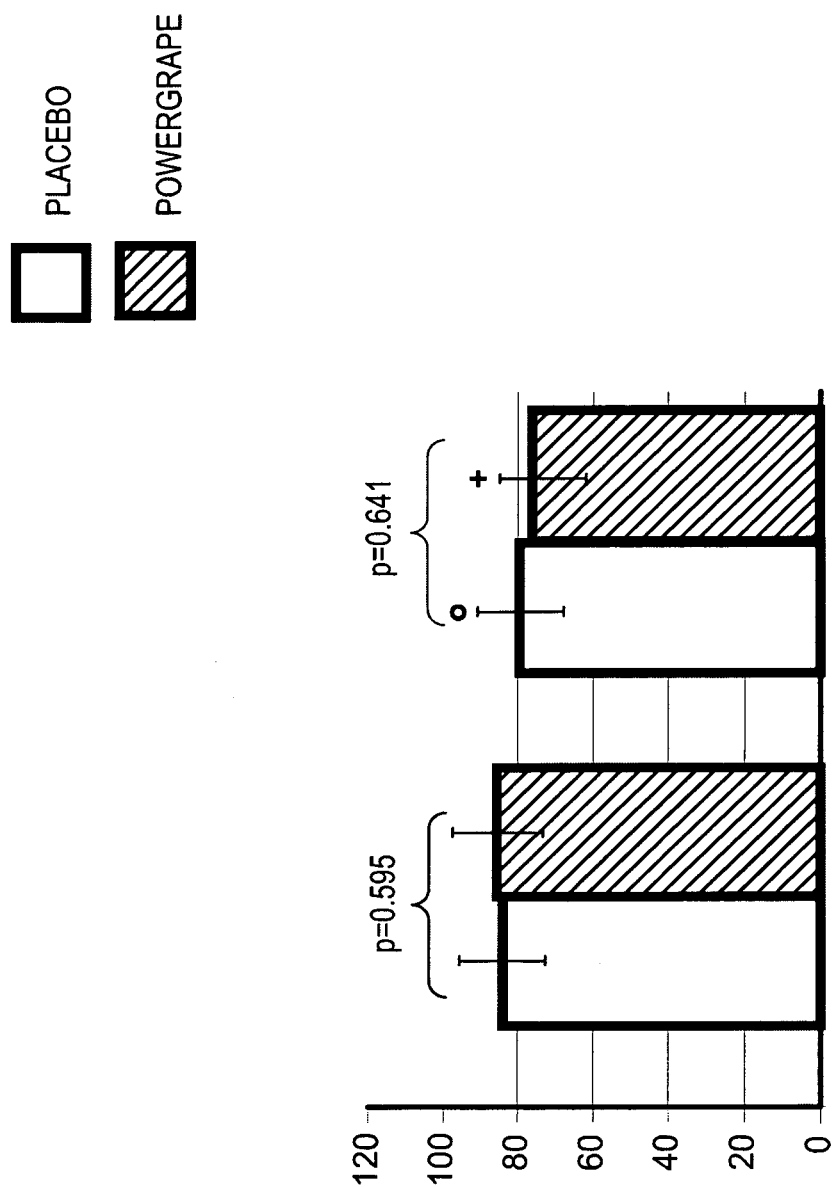
FIG. 11 illustrates a Ferritin level in plasma of athlete volunteers before (1$^{st}$ visit) and after (2$^{nd}$ visit) grape extract supplementation relative to a placebo.
Figure 12:
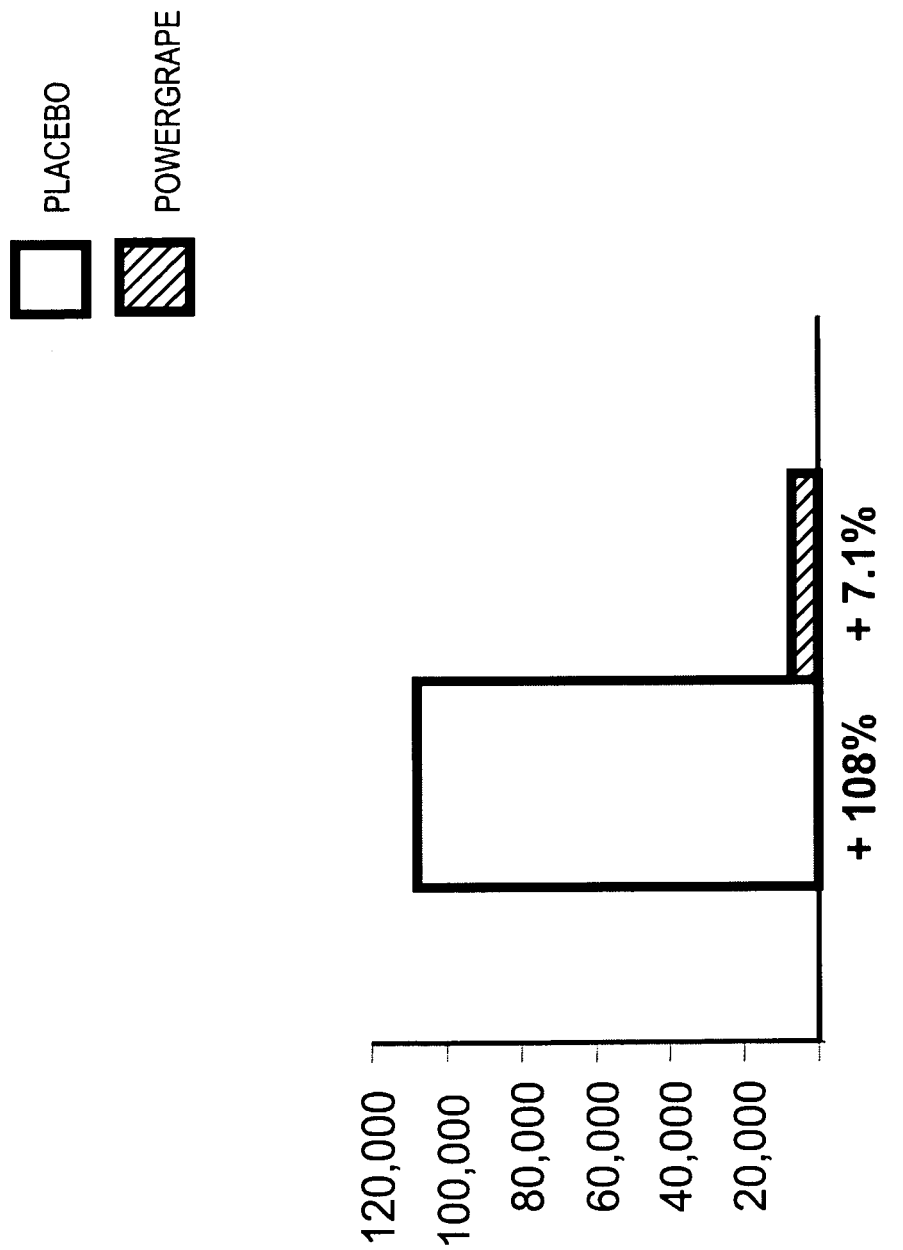
FIG. 12 illustrates a percentage of CPK variation in plasma of athlete volunteers after grape extract supplementation relative to a placebo.
Figure 13:
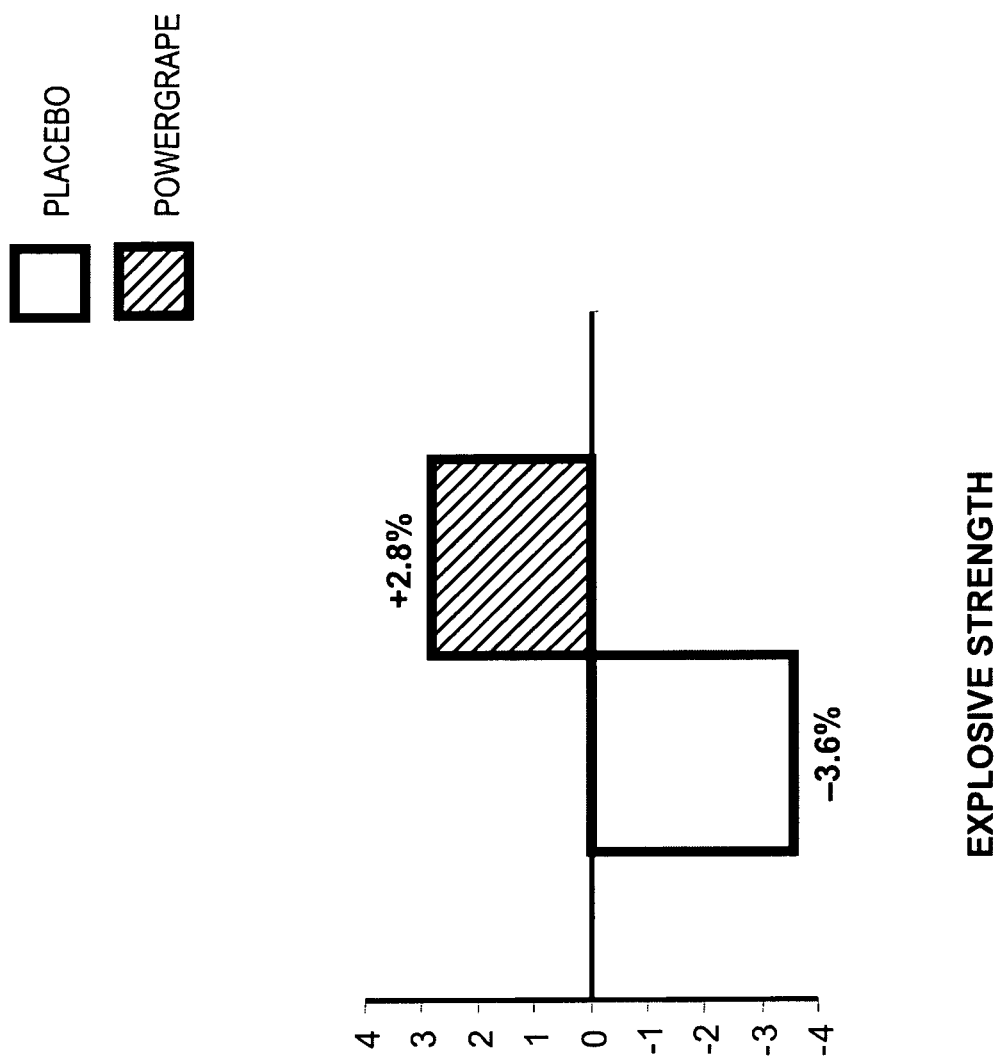
FIG. 13 illustrates measured explosive strength of athlete volunteers after grape extract supplementation relative to a placebo.
Figure 14:
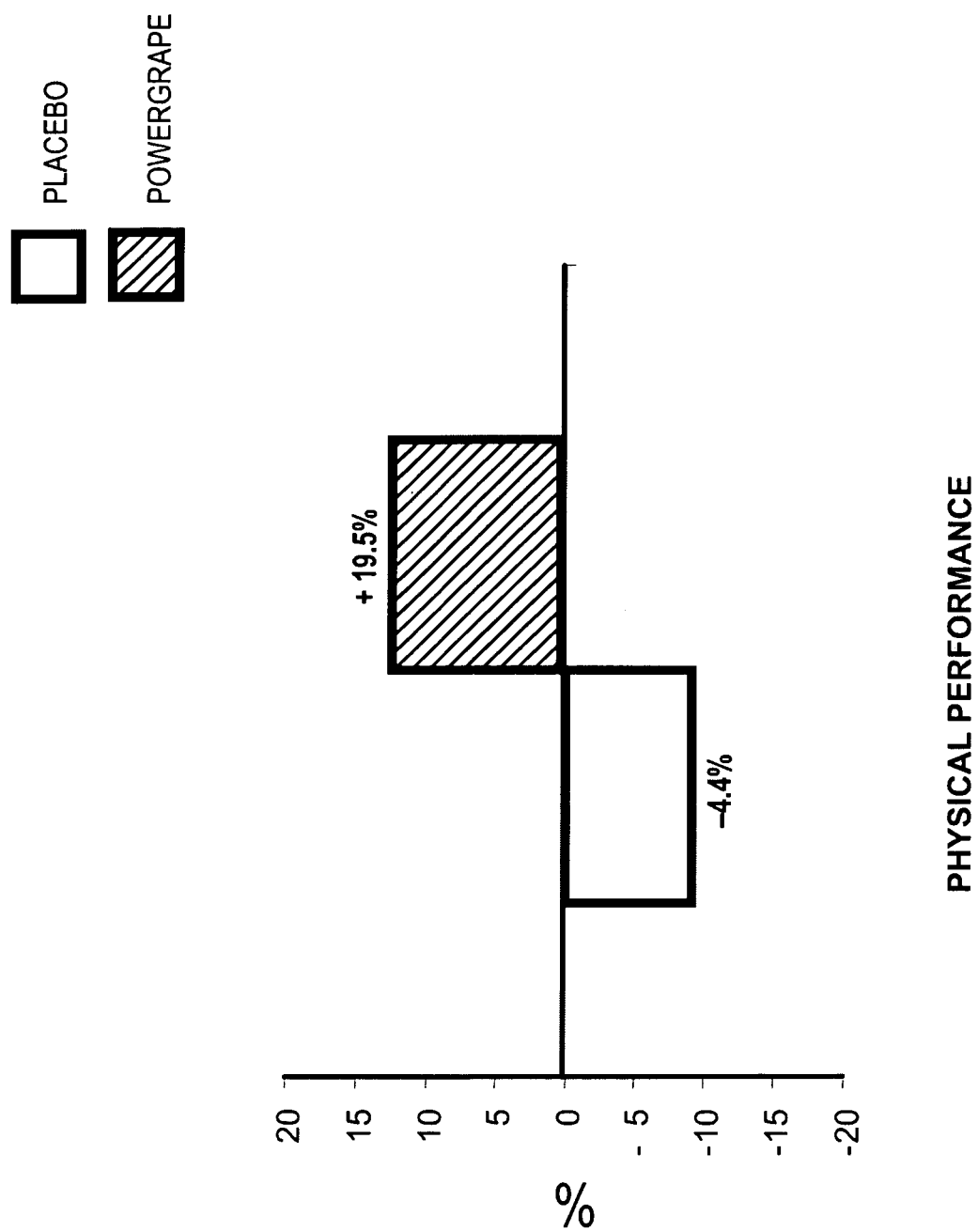
FIG. 14 illustrates a measurement of physical performance of athlete volunteers after grape extract supplementation relative to a placebo.
Figure 15:
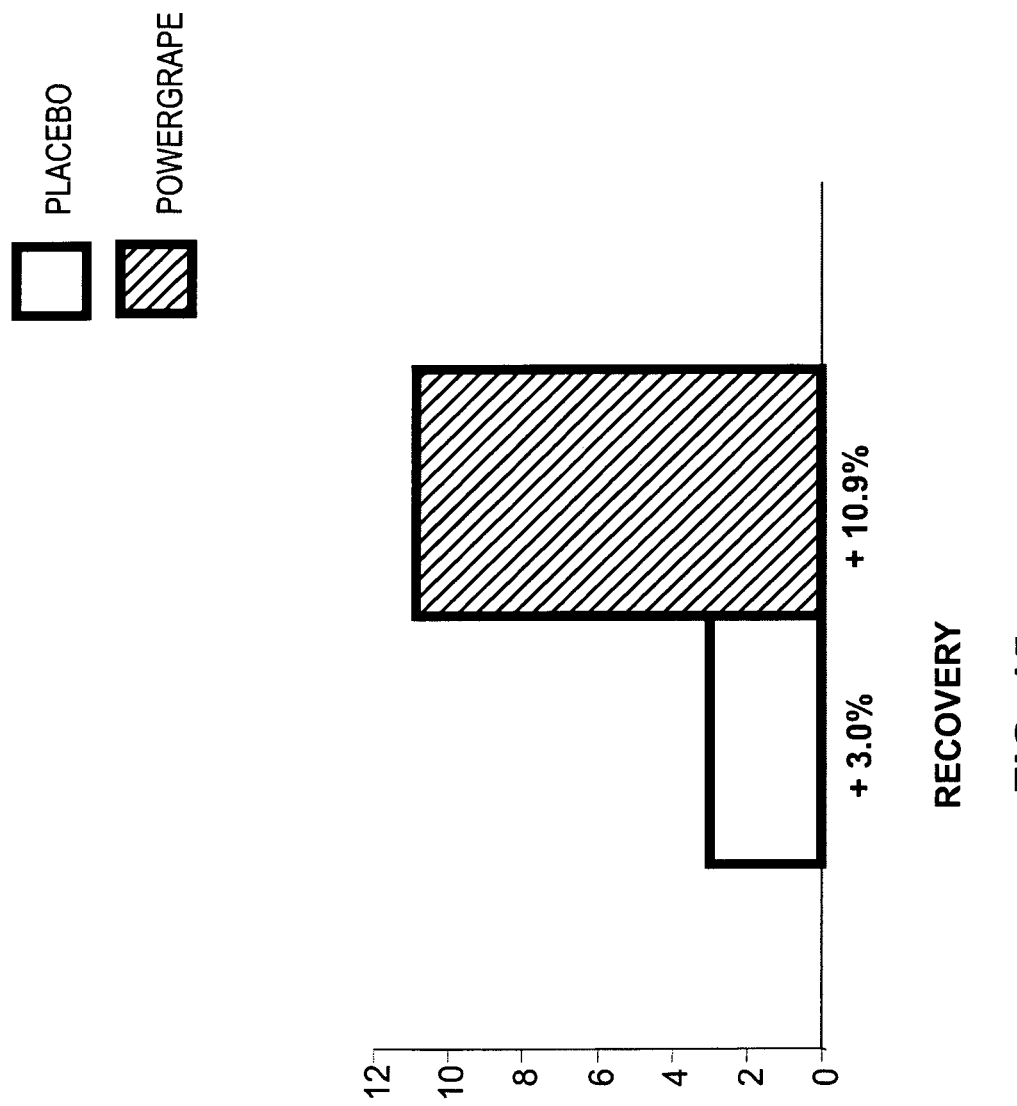
FIG. 15 illustrates recovery of athlete volunteers before (1$^{st}$ visit) and after (2$^{nd}$ visit) grape extract supplementation relative to a placebo.

Results show that grape extract administration (Powergrape™ grape extract, NATUREX) significantly increases the ORAC value in more than 10% (FIG. 4), limits the decrease of the FRAP value (FIG. 5), significantly decreases the urinary isoprostanes by more than 48% (FIG. 6), limits the decrease of glutathione peroxidase (FIG. 7), improves the level of vitamin E (FIG. 8), enhances the ratio of Vitamin E/cholesterol (FIG. 9), significantly increases the level of hemoglobin after the second visit (FIG. 10), does not modify the concentration of ferritin (FIG. 11), and reduces the level of creatine phosphokinase (CPK) (FIG. 12). Significantly, the Optojump® results showed unexpected results in that the explosive strength, physical performance, and recovery were increased through the application of the grape extract (FIGS. 13, 14 and 15). It should be understood that the effective amount of the grape extract can vary depending upon the weight of the person taking the treatment, as is known to persons of ordinary skill in the art. Further, the grape extract may be delivered by any conventional medium, in a formulation resulting in a liquid, powder, or caplet, tablet or capsule or other conventional medicament form, together with such fillers, additives, binders, excipients flavors and the like, as are commonly used in over-the-counter pharmaceutical and dietary supplement products.

One skilled in the art will appreciate that the present invention can be embodied in other forms than the examples recited, and the numerical quantities and ranges given, which are provided for purposes of illustration, and not of limitation.

We claim:

1. A method of enhancing physical performance during physical exercise of a human subject in need thereof, the method comprising:
providing a grape extract comprising 2.51% of gallic acid ± a standard deviation of 1.33% and 1.77% of procyanidin B2-O-gallate ± a standard deviation of 0.76%; and
administering to said human subject an amount of said grape extract effective to enhance physical performance during physical exercise;
wherein administering said amount comprises administering a dosage from about 100 mg to about 1,000 mg per day of said grape extract.

2. A method of enhancing physical performance during physical exercise of a human subject in need thereof, the method comprising:
providing a grape extract comprising 2.51% of gallic acid ± a standard deviation of 1.33% and 1.77% of procyanidin B2-O-gallate ± a standard deviation of 0.76%; and
administering to said human subject an amount of said grape extract effective to enhance physical performance during physical exercise;
wherein administering said amount comprises administering a dosage of 400 mg per day of said grape extract.

3. A method for enhancing explosive strength during physical exercise of a human subject in need thereof, the method comprising:
providing a grape extract comprising 2.51% of gallic acid ± a standard deviation of 1.33% and 1.77% of procyanidin B2-O-gallate ± a standard deviation of 0.76%; and
administering to said human subject an amount of said grape extract effective to enhance explosive strength during physical exercise;
wherein administering said amount comprises administering a dosage from about 100 mg to about 1,000 mg per day of said grape extract.

4. A method for enhancing explosive strength during physical exercise of a human subject in need thereof, the method comprising:
providing a grape extract comprising 2.51% of gallic acid ± a standard deviation of 1.33% and 1.77% of procyanidin B2-O-gallate ± a standard deviation of 0.76%; and
administering to said human subject an amount of said grape extract effective to enhance explosive strength during physical exercise;
wherein administering said amount comprises administering a dosage of 400 mg per day of said grape extract.

5. A method for enhancing recovery after physical exercise of a human subject in need thereof, the method comprising:
providing a grape extract comprising 2.51% of gallic acid ± a standard deviation of 1.33% and 1.77% of procyanidin B2-O-gallate ± a standard deviation of 0.76%; and
administering to said human subject an amount of said grape extract effective to enhance recovery after physical exercise;
wherein administering said amount comprises administering a dosage from about 100 mg to about 1,000 mg per day of said grape extract.

6. A method for enhancing recovery after physical exercise of a human subject in need thereof, the method comprising:
providing a grape extract comprising 2.51% of gallic acid ± a standard deviation of 1.33% and 1.77% of procyanidin B2-O-gallate ± a standard deviation of 0.76%; and
administering to said human subject an amount of said grape extract effective to enhance recovery after physical exercise;
wherein administering said amount comprises administering a dosage of 400 mg per day of said grape extract.

* * * * *